US007538248B2

(12) United States Patent
Baik et al.

(10) Patent No.: US 7,538,248 B2
(45) Date of Patent: May 26, 2009

(54) AMINEOXIDE TYPE SURFACTANT AND DETERGENT COMPOSITION COMPRISING IT

(75) Inventors: In Sub Baik, Seoul (KR); In Shik Cho, Daejeon (KR); Gyeong Yup Ghi, Daejeon (KR); Dong Sung Han, Daejeon (KR)

(73) Assignee: Aekyung Industrial Co., Ltd. (KR)

( * ) Notice: Subject to any disclaimer, the term of this patent is extended or adjusted under 35 U.S.C. 154(b) by 0 days.

(21) Appl. No.: 11/842,918

(22) Filed: Aug. 21, 2007

(65) Prior Publication Data

US 2008/0039655 A1 Feb. 14, 2008

Related U.S. Application Data

(63) Continuation of application No. PCT/KR2006/000606, filed on Feb. 22, 2006.

(30) Foreign Application Priority Data

Feb. 22, 2005 (KR) ...................... 10-2005-0014317

(51) Int. Cl.
*C07C 291/00* (2006.01)
*C11D 3/00* (2006.01)

(52) U.S. Cl. ...................................... 564/297; 510/515

(58) Field of Classification Search ....................... None
See application file for complete search history.

(56) References Cited

U.S. PATENT DOCUMENTS 3,628,905 A * 12/1971 Kirschnek et al. .............. 8/543
5,714,448 A * 2/1998 Choy et al. ................. 510/181

FOREIGN PATENT DOCUMENTS

GB 1266082 A 3/1972

OTHER PUBLICATIONS

International Search Report (PCT/KR2006/000606), Jun. 5, 2006, 3 pages.

* cited by examiner

*Primary Examiner*—Karl J Puttlitz
(74) *Attorney, Agent, or Firm*—Park & Associates IP Law LLC

(57) ABSTRACT

An amine oxide type surfactant, which has excellent compatibility with an anionic or non-ionic surfactant having excellent detergency and shows excellent detergency and softening effect, is represented by the following formula 1:

[Formula 1]

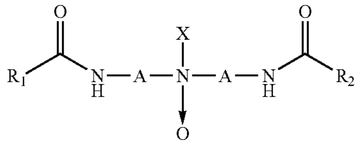

wherein $R_1$ and $R_2$ are the same or different, and each independently represents a $C_8$~$C_{22}$ linear or branched alkyl or alkenyl group; A represents a $C_1$~$C_4$ alkyl, alkenyl or hydroxyalkyl group; X represents OH, a $C_1$~$C_4$ alkyl, hydroxyalkyl, $(CH_2CH_2O)_nH$, $(CHCH_3CH_2O)_nH$ or a combination of $(CH_2CH_2O)_nH$ and $(CHCH_3CH_2O)_nH$; and n is a number of 1~30.

14 Claims, No Drawings

AMINEOXIDE TYPE SURFACTANT AND DETERGENT COMPOSITION COMPRISING IT

REFERENCE TO RELATED APPLICATIONS

This is a continuation of pending International Patent Application PCT/KR2006/000606 filed on Feb. 22, 2006, which designates the United States and claims priority of Korean Patent Application No. 10-2005-0014317 filed on Feb. 22, 2005.

FIELD OF THE INVENTION

The present invention relates to an amine oxide type surfactant having a dialkyl amide chain, which may be used for a detergent, and a detergent composition using the same. More particularly, the present invention relates to a surfactant having improved mildness, detergency, fabric softening effect and antistatic effect, and a detergent composition using the same.

BACKGROUND OF THE INVENTION

In general, a detergent is used for removing soils from fabrics, dishes, human bodies, and other articles. Hence, it is very important to ensure mildness of such detergents to the skin in the fields of all household goods, as detergents is to be in direct contact with the human body.

Therefore, many researches have been achieved to develop detergents having improved mildness in the related art. For example, there has been an effort to develop a surfactant having high biodegradability and mildness. As the detergent is based on surfactants in nature, development for an excellent surfactant results directly to a high-quality detergent. As a result of such researches, surfactants for improving biodegradability and mildness have been developed from alkylbenzene sulfonate (ABS), and particular examples thereof include linear alkylbenzene sulfonate (LAS), alpha-olefin sulfonate (AOS), alkyl ethoxylated sulfate (AES), or the like. More recently, alkyl polyglucoside (APG) as a sugar derivative has been developed. Additionally, in order to narrow the distribution of ethylene oxide (EO) addition mole numbers in nonionic surfactants, research and development for converting BRE (broad range ethoxylate) into NRE (narrow range ethoxylate) have been made. In general, as the proportion of a surfactant having a lower EO addition mole number increases in a nonionic surfactant, a detergent becomes have poor quality and becomes highly irritative. Therefore, the NRE technique is designed to reduce the proportion of ethoxylate having a low addition mole number of EO in the total surfactant composition.

In the result of past attempts, it was possible to improve the biodegradability and mildness of a surfactant compared with known surfactants. However, consumers might not be satisfied with such improvements. As past researches focused mainly on the improvement of biodegradability of a surfactant, mildness of a surfactant is hardly improved compared with known surfactants. Additionally, the developed surfactants are not cost-efficient.

It is generally accepted that the detergency and skin mildness (or softness) are contradictory properties of surfactant. Increased detergency is achieved by increasing the emulsifying efficiency, permeating activity and/or foam stability of a surfactant. However, increased detergency also results in the increased removal of protective component of skin and fabrics, along with contaminants. Such inconsistency between the detergency and skin mildness of surfactant is commonly applied to all types of detergents for household goods.

Recently, research and development for so-called softergent has been made intensively in order to have excellent detergency as well as excellent softening effect. However, such softergents are still unsatisfactory due to the aforementioned inconsistency between detergency and mildness. Therefore, many researches have been made since 1970's to solve the above problems and to develop a excellent quality softergent.

Japanese Patent Publication No. Sho56-21795, Japanese Patent Application No. Sho53-53478 and U.S. Pat. No. 4,961,866 disclose detergents using clay, such as bentonite, montmorillonite, or the like, as a softening ingredient. Such detergents had been developed from 1970's to early 1990's. The detergents are characterized by showing an improved softening effect by the accumulation of the clay on fabrics, while not adversely affecting the detergency. However, the detergents still have a poor softening effect comparing to the detergents using a separate fabric softener.

U.S. Pat. No. 5,863,887 discloses a detergent using a tertiary amine as a softening ingredient, instead of a cationic surfactant that interacts with an anionic surfactant, so as to prevent reduction of detergency.

Meanwhile, Japanese Patent Publication No. Hei7-286195 and U.S. Pat. No. 4,141,841 disclose a detergent that uses a cationic surfactant as a softening ingredient and further uses a non-ionic surfactant alone as a cleaning ingredient so as to prevent reduction of detergency, caused by the interaction between the cationic and anionic surfactant, and a detergent that minimizes detergency reduction by inhibiting the dispersibility of the cationic surfactants.

More recently, Japanese Patent Publication Nos. 2001-48851 and 2002-60789 and U.S. Pat. No. 4,095,946 disclose cationic softening ingredients modified from a known cationic surfactants, and particular examples of the modified softening ingredients include alkyldiammonium type, gemini type and polymer type surfactants. Such modified surfactants are characterized in that they do not reduce detergency and show an improved softening effect by virtue of their modified structures, as compared with known quaternary ammonium type cationic surfactants.

As described above, studies that have been made up to date focus on the minimization of the reduction of detergency of a detergent, caused by the mechanism of detergency/softening effect. However, it was not possible to solve the problem fundamentally.

SUMMARY OF THE INVENTION

Therefore, the present invention has been made in view of the above-mentioned problems. It is an object of the present invention to provide an amine oxide type surfactant having excellent detergency and softening effect with compatibility with anionic surfactants having an excellent detergency.

It is another object of the present invention to provide a detergent composition having a fabric softening effect as well as detergency, which comprises the above amine oxide type surfactant.

According to an aspect of the present invention, there is provided an amine oxide type surfactant represented by the following formula 1:

[Formula 1]

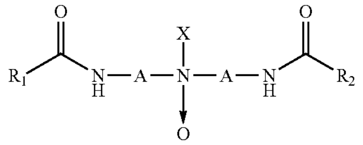

wherein $R_1$ and $R_2$ are the same or different, and each independently represents a $C_8$~$C_{22}$ linear or branched alkyl or alkenyl group; A represents a $C_1$~$C_4$ alkyl, alkenyl or hydroxyalkyl group; X represents OH, a $C_1$~$C_4$ alkyl, hydroxyalkyl, $(CH_2CH_2O)_nH$, $(CHCH_3CH_2O)_nH$ or a combination of $(CH_2CH_2O)_nH$ and $(CHCH_3CH_2O)_nH$; and n is a number of 1~30.

Preferably, each of $R_1$ and $R_2$ is a $C_{10}$~$C_{20}$ linear or branched alkyl or alkenyl group, and particular examples of $R_1CO$— and $R_2CO$— include lauroyl, myristoyl, palmitoyl, stearoyl, lauroleoyl, myristoleoyl, palmitolenoyl, oleoyl, linoeloyl, linolenoyl, or the like.

The amine oxide type surfactant represented by the above formula 1 either alone or a mixture of two or more of the amine oxide type surfactant represented by the above formula 1.

As the amine oxide type surfactant is the bulky amphoteric surfactant, not a cationic surfactant or an amine type softening compound, the amine oxide type surfactant can serve as a dual-function surfactant by a single molecule through the interconversion of cleaning effect/softening effect depending on pH variations.

Actually, in a general laundry process, cleaning is accomplished in an alkaline condition, pH decreases gradually after rinsing steps, and then softening is accomplished in a neutral condition. In the present invention, the surfactant shows not only detergency but also softening effect. That's because the surfactant shows characteristics of a non-ionic surfactant in an alkaline condition, while showing characteristics of a cationic surfactant in a neutral condition. Therefore, the surfactant according to the present invention can show not only detergency but also softening effect depending on pH variations. Additionally, the surfactant according to the present invention can show an increased adsorption power during a softening step due to its bulky molecular structure.

Meanwhile, a conventional surfactant has a molecular weight of about 400~600, so that it infiltrates into the skin with ease. However, the surfactant according to the present invention is a macromolecule having a molecular weight of about 800~1,600, so that it hardly infiltrates into the skin. Moreover, the surfactant according to the present invention forms a coating film when adsorbed on the skin to perform skin-moisturizing and -protecting functions, and thus show an excellent skin-protecting effect.

According to an embodiment of the present invention, the amine oxide type surfactant may be prepared from an amine represented by the following formula 2:

[Formula 2]

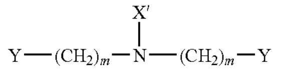

wherein X' includes —H, —OH, —$CH_3$ or —$(CH_2)_n$OH; n represents a number of 1~4; Y may represents —OH or —$NH_2$; and m represents a number of 2~4.

The amine compound represented by the above formula 2 forms an amide or an ester bond via the reaction with a fatty acid. The fatty acid that may be used in the present invention is a general $C_8$-$C_{22}$ saturated or unsaturated fatty acid, and particular examples thereof include saturated acids such as lauric acid, myristic acid, palmitic acid or stearic acid, and unsaturated fatty acids such as lauroleic acid, myristoleic acid, palmitolenic acid, oleic acid, linoleic acid or linolenic acid. The aforementioned fatty acids may be used alone or in combination.

The amine represented by the above formula 2 is allowed to react with a fatty acid in a molar ratio of about 1:1.6~2 at a temperature of 150~200° C. for 4~24 hours to form an amide or an ester bond.

[Formula 3]

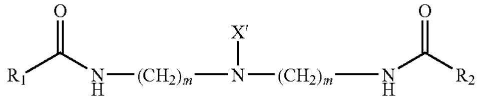

The compound represented by formula 3 represents a product after bonding with a fatty acid, particularly formed by an amide bond. In formula 3, each of $R_1$ and $R_2$ represents a $C_8$~$C_{22}$ linear or branched alkyl or alkenyl, and X' and m are the same as defined above.

When X' represents —OH or —H in the above formula 3, ethylene oxide (EO, —$CH_2CH_2O$) may be added to the compound represented by formula 3. Addition of EO to the compound represented by the above formula 3 is carried out in a molar ratio of the compound of formula 3 to EO of 1:1~30 under a pressure of 3~7 atm at a temperature of 120~200° C. During the addition of EO, a conventional alkali catalyst is used as a catalyst, and the reaction time depends on the molar ratio of reactants. Additionally, propylene oxide (PO, —$CHCH_3CH_2O$) may be further added to the compound represented by formula 3 in the same manner as described above, and addition of EO/PO may also be performed.

A compound represented by the following formula 4 represents a structure of the product obtained from the addition of EO to the compound represented by formula 3:

[Formula 4]

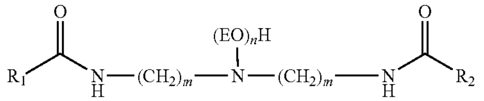

wherein n is a number of 1~30, and $R_1$, $R_2$ and m are the same as defined above. Because the hydrophilicity of the resultant product increases in proportion to the mole number of EO, it is possible to control the hydrophilicity/lipophilicity balance of the product through the variation of fat acids and its proportion and mole number of EO, or the like. Reaction of the compound represented by formula 4 with $H_2O_2$ provides an amine oxide compound represented by the following formula 5. The reaction condition is the same as a conventional reaction of an amine oxide. Additionally, when EO is not added to the compound represented by formula 3, i.e., when X' is —$CH_3$ in formula 3, the compound represented by formula 3 undergoes an amine oxide reaction to provide an amine oxide compound represented by the following formula 6.

The compound represented by formula 3 or 4 is allowed to react with $H_2O_2$ under general conditions by using $H_2O_2$ in an excessive amount of greater than the amount of the compound by about 5~10%. More particularly, the reaction temperature is maintained at 50~80° C., $H_2O_2$ is used in the form of a diluted solution containing 80~90% of water, which is introduced into the reaction system continuously for 2~8 hours, and the reaction is performed for 24~28 hours.

[Formula 5]

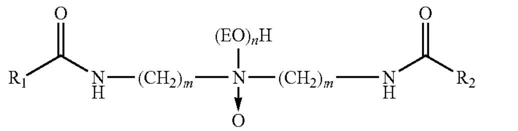

wherein n, m, $R_1$ and $R_2$ are the same as defined above.

[Formula 6]

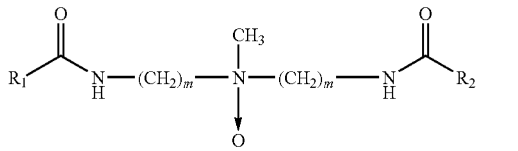

wherein m, $R_1$ and $R_2$ are the same as defined above.

The detergent composition according to the present invention comprises the amine oxide type surfactant represented by the above formula 1, which has detergency and softening effect at the same time. The amine oxide type surfactant is preferably used in the detergent composition in an amount of 0.01~40 wt % based on the total weight of the composition.

The detergent composition according to the present invention is characterized by comprising 0.01~40 wt % of the amine oxide type surfactant based on the weight of a detergent composition that comprises 5~50 wt % of a surfactant, such as a conventional non-ionic surfactant or anionic surfactant, and other additives.

The non-ionic surfactants that may be used include polyoxyalkylene alkyl ether, polyoxyalkylene alkyl phenol ether, polyoxyalkylene aryl phenol ether, polyoxyalkylene fatty acid ester, polyoxyalkylene sorbitan fatty acid ester, polyoxyalkylene alkyl amine, sorbitan fatty acid ester, alkyl alcohol amine or aryl alcohol amine. Particular examples thereof include adducts of 1~20 moles of ethylene oxide or ethylene oxide/propylene oxide to C8~C20 higher alcohols.

The anionic surfactants that may be used include sulfate ester of fatty alcohol, alkylbenzene sulfonates, alphaolefin sulfonates, alphasulfo fatty acid salts, or alkyl esters or fatty acid salts thereof.

The additives that may be used in the present invention include fragrances, pigments, fluorescence brighteners (stylbene type, biphenyl type, etc.), enzymes (protease, amylase, lipase, cellulase, etc.), moisturizing agents (glycerin, diglycerin, propylene glycol, dipropylene glycol, 1,3-butylene glycol, sorbitol, polyethylene glycol hyaluronic acid, etc.), pH modifiers (an acid or acidic salt including phosphoric acid, sodium dihydrogen phosphate, citric acid, tartaric acid, fumaric acid, etc.; or alkali compounds including trisodium phosphate, disodium hydrogenphosphate, dipotassium hydrogen phosphate, trisodium citrate, disodium succinate, etc.), various plant extracts, chelating agents, defoaming agents, antioxidants, preservatives, antibacterial agents, lower alcohols, polyhydric alcohols, or the like.

The detergent composition according to the present invention may take any form of solid, liquid, cream, powder and other forms, and may be prepared by a conventional method.

The surfactant according to the present invention may be applied to various types of detergents such as laundry detergents, softening agents and dishwashing detergents, cleansing agents such as shampoo, body cleanser and soap, cosmetic cleansing products and emulsifiers for cosmetic toner and lotion, etc.

The amine oxide type surfactant according to the present invention may be used in combination with a nonionic or anionic surfactant having excellent detergency, and can show excellent softening effect as well as excellent detergency.

DETAILED DESCRIPTION OF THE INVENTION

Reference will now be made in detail to the preferred embodiments of the present invention. It is to be understood that the following examples are illustrative only and the present invention is not limited thereto.

PREPARATION EXAMPLE 1

Synthesis of N-di-[3-(stearoylamino)propyl]-N-methylamine oxide

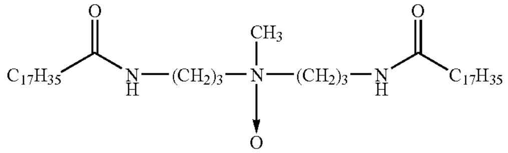

N-di(3-aminopropyl)-N-methylamine (200 g) was mixed with stearic acid (800 g) in a molar ratio of about 1:2, and the mixture was allowed to react at a temperature of 160° C. under nitrogen atmosphere for 3 hours to provide N-di[3-(stearoylamino)propyl]-N-methylamine. Then, 500 g of the N-di[3-(stearoylamino)propyl]-N-methylamime was allowed to react with 80 g of $H_2O_2$ (35%) to provide the title compound. The reaction condition was the same as a conventional reaction of amine oxide. Particularly, $H_2O_2$ was used in an amount greater than the stoichiometric amount by about 5~10%, the reaction temperature was maintained at 50~70° C., $H_2O_2$ was used in the form of a diluted solution comprising about 90% of water and was introduced into the reaction system continuously for 6 hours, and the reaction was performed at 70~80° C. for 24 hours.

NMR spectrum ($CDCl_3$, internal standard: TMS)

2.05 ppm (m, 4H, (—NO—$CH_2$—$CH_2$—$CH_2$—NHCO—))

2.2 ppm (t, 4H, (—$CH_2$—CONH—))

2.4 ppm (t, 4H, (—$CH_2$—NO—$CH_2$—))

3.1 ppm (s, 3H, ($CH_3$—NO—))

3.35 ppm (q, 4H, (CONH—$CH_2$—$CH_2$—$CH_2$—NO—$CH_2$—$CH_2$—$CH_2$—NHCO—))

7.8 ppm (t, 2H, (—CO—NH—)).

EXAMPLES 1 AND 2 AND COMPARATIVE EXAMPLES 1 AND 2

N-di-[3-(stearoylamino)propyl-N-methylamine oxide (DSA-AO) obtained from Preparation Example 1 was used to provide a detergent composition according to the formulation represented by the following Table 1, and the detergent was evaluated for its detergency and softening effect. The results are also shown in Table 1.

<Evaluation of Detergency>

Detergency of a detergent was evaluated by using an agitation/mixing type detergency tester (Tergotometer, United States Testing Co., Inc.), generally used in a laboratory. The test was carried out under the conditions of a temperature of 25° C., a rotation speed of 120 rpm, 1 g of sample in 1 L of water, washing time of 10 minutes and two rinsing cycles, each being 3 minutes long.

Soiled fabric used for the test was AS12 and Japanese wet soiled fabric. Each soiled fabric was cut into a size of 4 cm×4 cm and nine sheets of fabrics were used for a sample.

After washing, cleaning effect for each fabric was evaluated by measuring whiteness of each cloth with a calorimeter (Japan testing Co., Inc.). Then the detergency was calculated according to the following formula, and relative detergency of each detergent composition was shown on the basis of the detergency obtained from Comparative Example 1 (detergency=100).

$$\text{Detergency } (\%) = (C-B)/(A-B)*100$$

Wherein A is the whiteness of a white cloth, B is the whiteness of a soiled cloths before washing, and C is the whiteness of a soiled cloths after washing.

<Evaluation of Softening Effect>

Each of the surfactant compositions according to Examples 1 and 2 and Comparative Examples 1 and 2 was adjusted to a concentration of 35 g/35 L, and a commercially available 100% cotton towel was washed with each composition, and dried naturally. Then, the towel was evaluated sensually by an expert in the relevant art. Softening effect, evaluated by touch, was graded from 1 to 5. At least three evaluation cycles were performed for each composition and the average grade was shown by the following criteria.

| | |
|---|---|
| Softening Effect | Excellent (3.5 or higher)<br>Good (3.0~3.5)<br>Moderate (2.5~3.0)<br>Poor (2.5 or less) |

TABLE 1

| | | Ex. 1 | Ex. 2 | Comp. Ex. 1 | Comp. Ex. 2 | Softening treatment |
|---|---|---|---|---|---|---|
| Composition (wt %) | AEO(EO 9 mol) | 10 | 10 | 10 | 10 | — |
| | DSA-AO | 5 | 10 | — | — | — |
| | ESQ | — | — | — | 5 | — |
| | AOS | — | — | — | — | — |
| | water, pH modifier | balance | balance | balance | Balance | — |
| Detergency(%) | AS12 soiled fabric | 101 | 99 | 100 | 89 | — |
| | Japanese wet soiled fabric | 95 | 89 | 100 | 77 | |
| Softening effect | | 2.76 | 2.96 | 1.55 | 3.05 | 3.77 |

AEO (EO 9 mol): ethyl alcohol ethoxylate (primary laurylalcohol ethoxylate), addition mole number of ethylene oxide=9 mol.

ESQ: dialkylester type quaternary ammonium salt (available from Cognis Co.).

PREPARATION EXAMPLE 2

Synthesis of Mixed Amine Oxide Surfactant (DE12-OSA28-AO)

DE12-OSA28-AO represents a mixture of N-di-[2-(stearoylamino)ethyl]-N-polyoxyethylene amine oxide, N-[2-(stearoylamino)ethyl]-N-[2-(oleoylamino)ethyl]-N-polyoxyethylene amine oxide and N-di-[2-(oleoylamino) ethyl]-N-polyoxyethylene amine oxide. The compounds are represented by the following formulae:

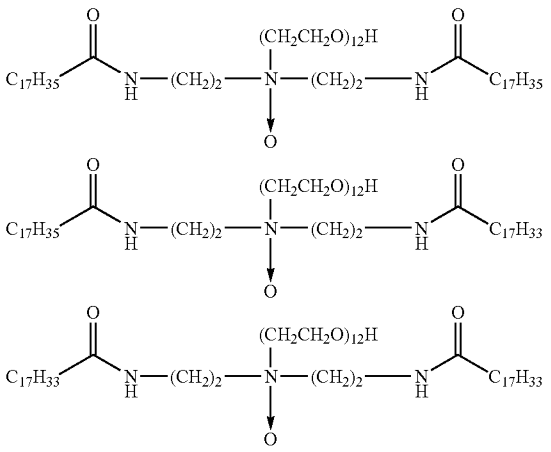

As a fatty acid, a mixture of stearic acid with oleic acid (molar ratio=8:2) was used. Then, 150 g of di-(2-aminoethyl) amine and 850 g of the fatty acid were allowed to react in a molar ratio of about 1:2 at a temperature of 160° C. under nitrogen atmosphere for 3 hours, while removing water from the reaction mixture. To the reaction mixture, ethylene oxide was added in a molar ratio of 1:12 and the resultant mixture was allowed to react by using an alkali catalyst (NaOH, KOH) under a pressure of 4□6 atm at a temperature of 120-140° C. for 4 hours. Next, 500 g of the ethylene oxide adduct of the amine was allowed to react with 50 g of $H_2O_2$ (35%) to obtain the title compound. The reaction condition was the same as a conventional reaction of amine oxide. Particularly, $H_2O_2$ was used in an amount greater than the stoichiometric amount by about 5-10%, the reaction temperature was maintained at 50-70° C., $H_2O_2$ was used in the form of a diluted solution comprising about 90% of water and was introduced into the reaction system continuously for 6 hours, and the reaction was performed at 70~80° C. for 24 hours.

NMR spectrum ($CDCl_3$, internal standard: TMS)

2.0 ppm (m, 8H, ($-CH_2-CH=CH-CH_2-$))

2.2 ppm (t, 4H, ($-CH_2-CONH-$))

2.6 ppm (t, 4H, ($-CH_2-NO-CH_2-$))

3.3 ppm (q, 4H, ($-CONH-CH_2-CH_2-NO-CH_2-CH_2-NHCO-$))

3.65 ppm (m, 48H, ($-NO-(CH_2-CH_2-O-)_{12}H$))

5.4 ppm (m, 4H, ($-CH_2-CH=CH-CH_2-$))

6.9 ppm (t, 2H, ($-CO-NH-$)).

EXAMPLES 3-10 AND COMPARATIVE EXAMPLES 3-6

The mixed amine oxide surfactant (DE12-OSA28-AO) obtained from Preparation Example 2 was used to prepare the detergent compositions as shown in the following Tables 2 and 3, and each detergent composition was evaluated for its detergency and softening effect. The results are also shown in Tables 2 and 3.

TABLE 2

| | | Ex. 3 | Ex. 4 | Ex. 5 | Ex. 6 | Comp. Ex. 3 | Comp. Ex. 4 | Softening treatment |
|---|---|---|---|---|---|---|---|---|
| Composition (wt %) | AEO(EO 9 mol) | 10 | 10 | 10 | 10 | 10 | 10 | — |
| | DE5-OSA28-AO | 5 | — | — | — | — | — | |
| | DE7-OSA28-AO | — | 5 | — | — | — | — | |
| | DE9-OSA28-AO | — | — | 5 | — | — | — | — |
| | DE12-OSA28-AO | — | — | — | 5 | — | — | — |
| | ESQ | — | — | — | — | — | 5 | — |
| | water, pH modifier | balance | balance | balance | balance | balance | balance | — |
| Detergency (%) | AS12 soiled fabric | 99 | 100 | 98 | 101 | 100 | 90 | |
| | Japanese wet soiled fabric | 95 | 98 | 94 | 98 | 100 | 76 | |
| Softening effect | | 2.81 | 2.93 | 2.45 | 2.14 | 1.45 | 3.14 | 3.81 |

TABLE 3

| | | Ex. 7 | Ex. 8 | Ex. 9 | Ex. 10 | Comp. Ex. 5 | Comp. Ex. 6 | Softening treatment |
|---|---|---|---|---|---|---|---|---|
| Composition (wt %) | AOS | 10 | 10 | 10 | 10 | 10 | 10 | — |
| | DE5-OSA28-AO | 5 | — | | — | — | — | — |
| | DE7-OSA28-AO | — | 5 | — | | — | — | — |
| | DE9-OSA28-AO | — | — | 5 | — | — | — | — |
| | DE12-OSA28-AO | — | — | — | 5 | — | — | — |
| | ESQ | — | — | — | — | — | 5 | — |
| | water, pH modifier | balance | Balance | balance | balance | balance | balance | — |
| Detergency (%) | AS12 soiled fabric | 98 | 101 | 97 | 99 | 100 | 87 | |
| | Japanese wet soiled fabric | 99 | 99 | 95 | 96 | 100 | 72 | |
| Softening effect | | 2.31 | 2.71 | 2.84 | 2.21 | 1.81 | 1.52 | 3.76 |

DE5-OSA28-A0, DE7-OSA28-A0 and DE9-OSA28-AO: Mixed amine oxide surfactants obtained by the same method as DE12-OSA28-AO according to Preparation Example 2, except that addition mole numbers of ethylene oxide are 5 moles, 7 moles and 9 moles, respectively.

AOS: alphaolefin sulfonate salt.

INDUSTRIAL APPLICABILITY

As can be seen from Tables 1, 2 and 3, the amine oxide type surfactant according to the present invention can provide an excellent softening effect while not reducing the detergency, even when it is used in combination with a non-ionic or anionic surfactant having excellent detergency.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

What is claimed is:

1. A laundry detergent composition for washing a fabric comprising an amine oxide type surfactant represented by the following formula 1:

(Formula 1)

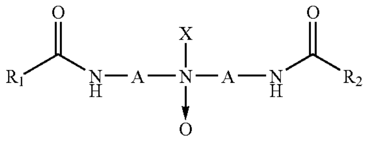

wherein $R_1$ and $R_2$ are the same or different, and each independently represents a $C_8$~$C_{22}$ linear or branched alkyl or alkenyl group; A represents a $C_1$~$C_4$ alkyl, alkenyl or hydroxyalkyl group; X represents $(CH_2CH_2O)_nH$, $(CHCH_3CH_2O)_nH$ or a combination of $(CH_2CH_2O)_nH$ and $(CHCH_3CH_2O)_nH$; and n is a number of 2-30.

2. The laundry detergent composition of claim 1, wherein each of $R_1$ and $R_2$ is a $C_{10}$~$C_{20}$ linear or branched alkenyl group.

3. The laundry detergent composition of claim 2, wherein each of $R_1CO$— and $R_2CO$— is selected from the group consisting of lauroyl, myristoyl, palmitoyl, stearoyl, lauroleoyl, myristoleoyl, palmitolenoyl, oleoyl, linoeloyl, and linolenoyl.

4. The laundry detergent composition of claim 1, wherein the amine oxide type surfactant is N-di-[3-(stearoylamino) propyl]-N-methylamine oxide, N-di-[2-(stearoylamino) ethyl]-N-polyoxyethylene amine oxide, N-[2-(stearoylamino)ethyl]-N-[2-(oleoylamino) ethyl]-N-polyoxyethylene amine oxide, and N-di-[2-(oleoylamino) ethyl]-N-polyoxyethylene amine oxide.

5. The laundry detergent composition of claim 1, wherein the composition further comprises adducts of 1~20 moles of ethylene oxide or ethylene oxide/propylene oxide to $C_8$~$C_{20}$ higher alcohol.

6. The laundry detergent composition of claim 5, wherein the amine oxide type surfactant is present in an amount of 5% or 10% by weight of the composition and the adducts of 1~20 moles of ethylene oxide or ethylene oxide/propylene oxide to $C_8$~$C_{20}$ higher alcohol is present in an amount of 10% by weight of the composition.

7. The laundry detergent composition of claim 1, wherein the composition provides a softening effect without reduced detergency to the fabric when washed with the composition.

8. The laundry detergent composition of claim 5, wherein the composition provides a softening effect without reduced detergency to the fabric when washed with the composition.

9. The laundry detergent composition of claim 1, wherein n is a number of 12.

10. The laundry detergent composition of claim 1, wherein X represents (EO)nH.

11. The laundry detergent composition of claim 5, wherein n is a number of 12.

12. The laundry detergent composition of claim 5, wherein X represents (EO)nH.

13. A method of cleaning and softening a fabric which comprises washing the fabric with the detergent composition of claim 1.

14. A method of cleaning and softening a fabric which comprises washing the fabric with the detergent composition of claim 5.

* * * * *